(12) United States Patent
Rogers

(10) Patent No.: US 10,468,150 B2
(45) Date of Patent: Nov. 5, 2019

(54) ELECTRON COLLECTOR, IMAGING SYSTEM AND METHOD OF MANUFACTURE

(71) Applicant: GENERAL ELECTRIC COMPANY, Schenectady, NY (US)

(72) Inventor: Carey Shawn Rogers, Waukesha, WI (US)

(73) Assignee: General Electric Company, Schenectady, NY (US)

(*) Notice: Subject to any disclaimer, the term of this patent is extended or adjusted under 35 U.S.C. 154(b) by 262 days.

(21) Appl. No.: 15/626,649

(22) Filed: Jun. 19, 2017

(65) Prior Publication Data
US 2018/0366237 A1 Dec. 20, 2018

(51) Int. Cl.
| | |
|---|---|
| *H01J 5/18* | (2006.01) |
| *G21K 1/10* | (2006.01) |
| *H01J 35/08* | (2006.01) |
| *H01J 35/06* | (2006.01) |
| *G21K 1/02* | (2006.01) |
| *H01J 35/14* | (2006.01) |
| *H01J 35/16* | (2006.01) |
| *A61B 6/10* | (2006.01) |
| *A61B 6/00* | (2006.01) |
| *A61B 6/03* | (2006.01) |

(52) U.S. Cl.
CPC ............... *G21K 1/10* (2013.01); *A61B 6/107* (2013.01); *A61B 6/40* (2013.01); *G21K 1/02* (2013.01); *H01J 35/06* (2013.01); *H01J 35/08* (2013.01); *H01J 35/14* (2013.01); *H01J 35/16* (2013.01); *A61B 6/032* (2013.01); *A61B 6/4488* (2013.01)

(58) Field of Classification Search
CPC ... G21K 1/10; G21K 1/02; H01J 35/08; H01J 35/06; H01J 35/14; H01J 35/16; H01J 2235/1216; H01J 2235/16; A61B 6/032
See application file for complete search history.

(56) References Cited

U.S. PATENT DOCUMENTS

| | | |
|---|---|---|
| 5,995,585 A | 11/1999 | Salasoo |
| 6,215,852 B1 | 4/2001 | Rogers et al. |
| 6,301,332 B1 | 10/2001 | Rogers et al. |
| 6,714,626 B1 | 3/2004 | Subraya et al. |
| 6,980,628 B2 | 12/2005 | Wang et al. |
| 7,410,296 B2 | 8/2008 | Rogers |
| 2004/0114724 A1* | 6/2004 | Subraya ............... H01J 35/18 378/141 |
| 2009/0279669 A1* | 11/2009 | Allen ................. H01J 35/16 378/140 |
| 2012/0099701 A1* | 4/2012 | Rogers ................ H01J 35/14 378/62 |
| 2013/0156161 A1* | 6/2013 | Andrews ............. H01J 35/16 378/140 |

* cited by examiner

*Primary Examiner* — Kiho Kim

(57) ABSTRACT

An electron collector for an electromagnetic ray generating device is provided. The electron collector includes a body having a surface configured to intercept backscattered electrons produced by an electron beam striking an anode to generate electromagnetic rays. The body is operative to absorb the backscattered electrons and is formed by particles of a first material disposed within a matrix of a second material.

18 Claims, 9 Drawing Sheets

ELECTRON COLLECTOR, IMAGING SYSTEM AND METHOD OF MANUFACTURE

BACKGROUND

Technical Field

Embodiments of the invention relate generally to medical imaging systems, and more specifically, to an electron collector, imaging system and method of manufacturing the same.

Discussion of Art

Many imaging systems utilize x-ray tubes to generate images of an object. X-ray tubes generally include a cathode disposed at a distance from an anode within a vacuum vessel. The anode usually includes an impact zone that is generally fabricated from a refractory metal with a high atomic number, such as tungsten or tungsten alloy. A voltage difference is maintained between the cathode and the anode such that an electron beam is generated by the cathode and strikes the anode within the impact zone, typically called the focal spot. As electrons within the electron beam impact the anode, their kinetic energy is converted to high-energy electromagnetic radiation, e.g., x-rays.

In many such x-ray tubes, a relatively large percentage of the electrons that strike the anode "backscatter," which, as used herein, refers to the deflection of electrons by the anode. Backscattered electrons can re-impact the anode and produce off-focus x-rays that diminish x-ray image quality. For example, a significant fraction of backscattered electrons may be pulled back to the anode in a bi-polar x-ray tube where the anode is maintained at positive potential relative to ground. Additionally, backscattered electrons can also interact with other internal components of the x-ray tube so as to transfer kinetic energy in the form of heat. Excess heat generation within an x-ray tube, however, may adversely affect the durability of, and/or increase expenses associated with providing additional cooling capacity for, the x-ray tube.

Accordingly, some x-ray tubes utilize electron collectors, which are typically shell like structures that partially and/or fully surround the focal spot on the anode, to absorb backscattered electrons, convert the kinetic energy of the absorbed backscattered electrons into heat, and transfer/conduct the heat out of the x-ray tube. Many electron collectors also serve as collimators with respect to the electromagnetic rays generated from the electron beam striking the anode.

As it happens to be, however, many materials good at conducting heat, e.g., copper, usually fail to attenuate electromagnetic rays adequately for use in collimators, while many materials good at attenuating electromagnetic rays, e.g., tungsten and molybdenum, are more expensive than copper and not as good thermal conductors. Thus, the bodies of many electron collectors are often made primarily from materials which are good at attenuating electromagnetic rays, while incorporating separate heat exchanging/transferring components made from materials good at conducting heat; or constructed from materials with high thermal conductivity, but having relatively poor x-ray attenuating ability. In other words, many electron collectors have different components for electron collection/radiation collimation and heat exchanging. For example, some electron collectors have bodies made from molybdenum with external copper heat exchangers mounted thereto or fabricated into the body by traditional machining methods.

Traditional methods of mounting and/or fabricating such heat exchangers onto/into the body of an electron collector typically involve the creation of brazed joints between the heat exchanging components and the body of the electron collector. Brazed joints, however, can be complex and may reduce the efficiency of the heat exchanging components to conduct heat away from the body of the electron collector due to unwetted zones in the joint (i.e. voids). Moreover, the body and the heat exchanging components are usually fabricated/constructed in separate processes.

What is needed, therefore, is an improved electron collector, imaging system and method of manufacturing the same.

BRIEF DESCRIPTION

In an embodiment, an electron collector for an electromagnetic ray generating device is provided. The electron collector includes a body having a surface configured to intercept backscattered electrons produced by an electron beam striking an anode to generate electromagnetic rays. The body is operative to absorb the backscattered electrons and is formed by particles of a first material disposed within a matrix of a second material.

In another embodiment, an electromagnetic ray generating system is provided. The system includes an anode, a cathode, and an electron collector. The cathode is operative to generate an electron beam that strikes the anode to generate electromagnetic rays; and the electron collector is operative to absorb backscattered electrons produced by the electron beam striking the anode, and is formed by particles of a first material disposed within a matrix of a second material.

In yet another embodiment, an electromagnetic ray generating system is provided. The system includes a vacuum enclosure, an anode disposed within the vacuum enclosure; a cathode disposed within the vacuum enclosure, and an electron collector disposed within the vacuum enclosure. The cathode is operative to generate an electron beam that strikes the anode to generate electromagnetic rays; and the electron collector is operative to absorb backscattered electrons produced by the electron beam striking the anode, and is formed by particles of a first material disposed within a matrix of a second material.

In yet still another embodiment, a method of manufacturing an electron collector is provided. The method includes forming a base structure by depositing one or more layers of particles of a first material onto a substrate. The one or more layers are bound together via a binding agent deposited in-between adjacent layers of the one or more layers, and the base structure includes a surface configured to intercept backscattered electrons produced by an electron beam striking an anode to generate electromagnetic rays. The method further includes removing some of the binding agent from the base structure such that the base structure is porous. The method further includes forming a body of the electron collector by infiltrating the porous base structure with a second material such that the second material forms a matrix with the particles of the first material disposed therein. The body is operative to absorb the backscattered electrons.

DRAWINGS

The present invention will be better understood from reading the following description of non-limiting embodiments, with reference to the attached drawings, wherein below:

Figure 1:
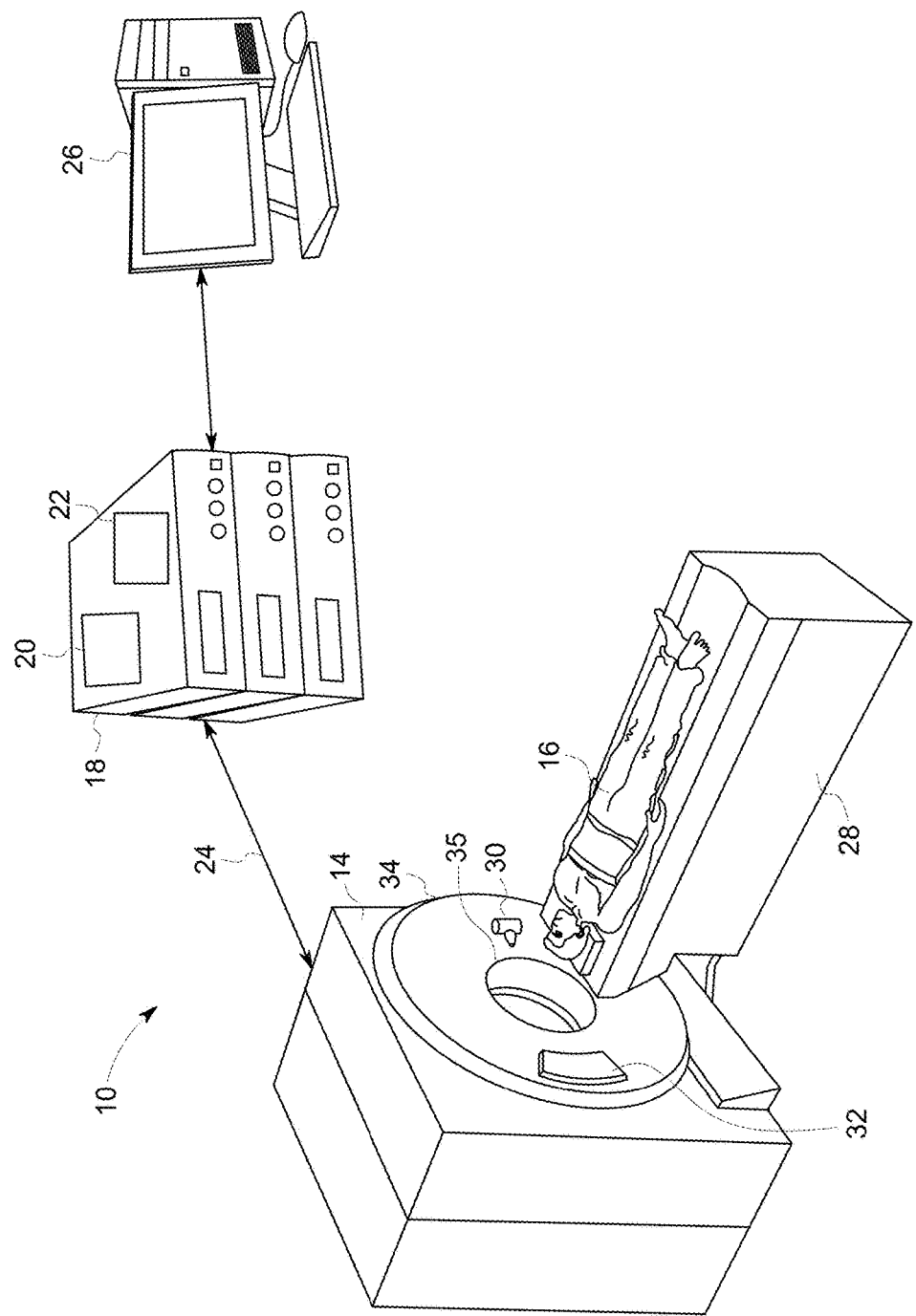
FIG. 1 is a schematic diagram of an imaging system that includes an electromagnetic ray generator having an electron collector, in accordance with an embodiment of the present invention.
Figure 4:
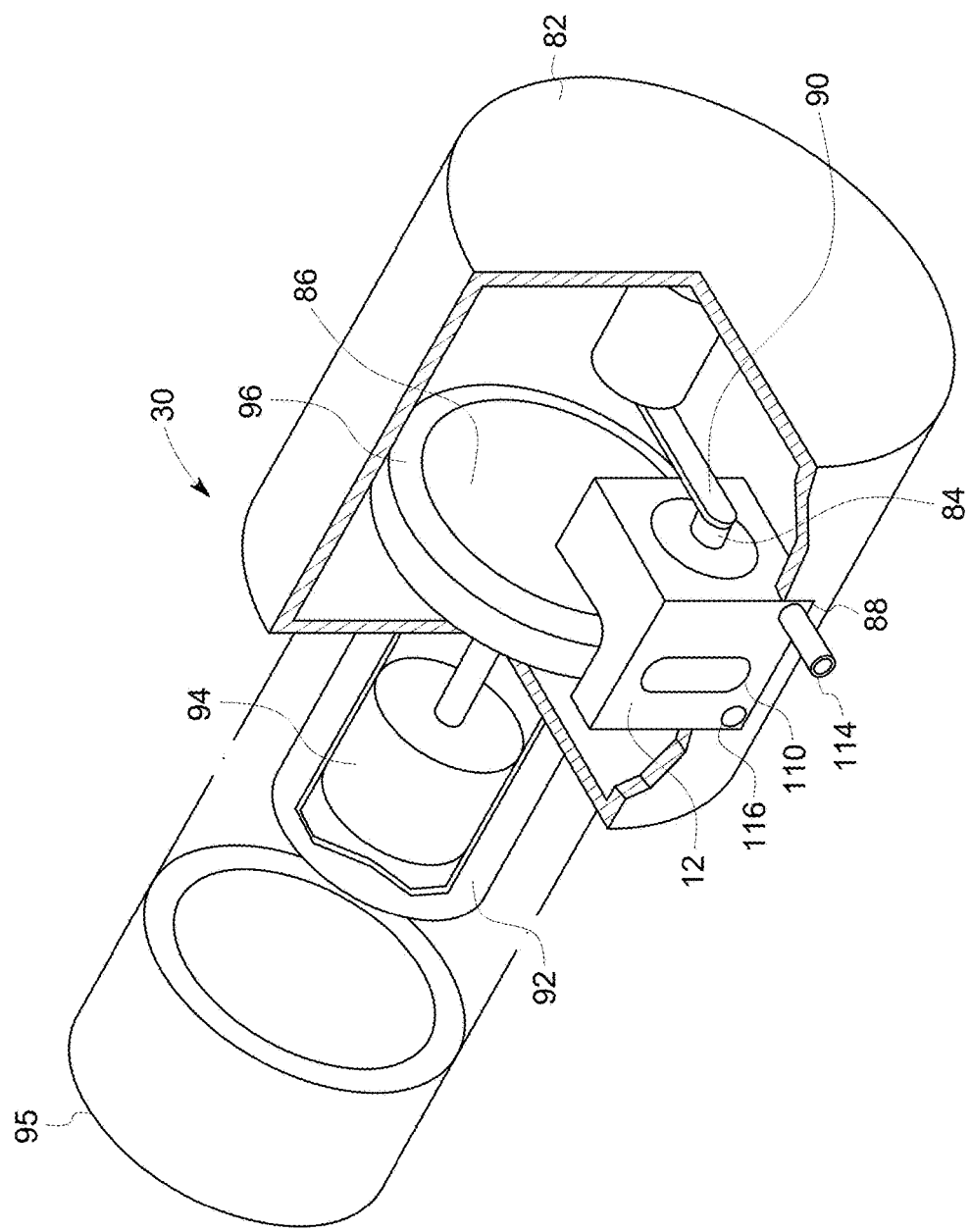
Figure 5:
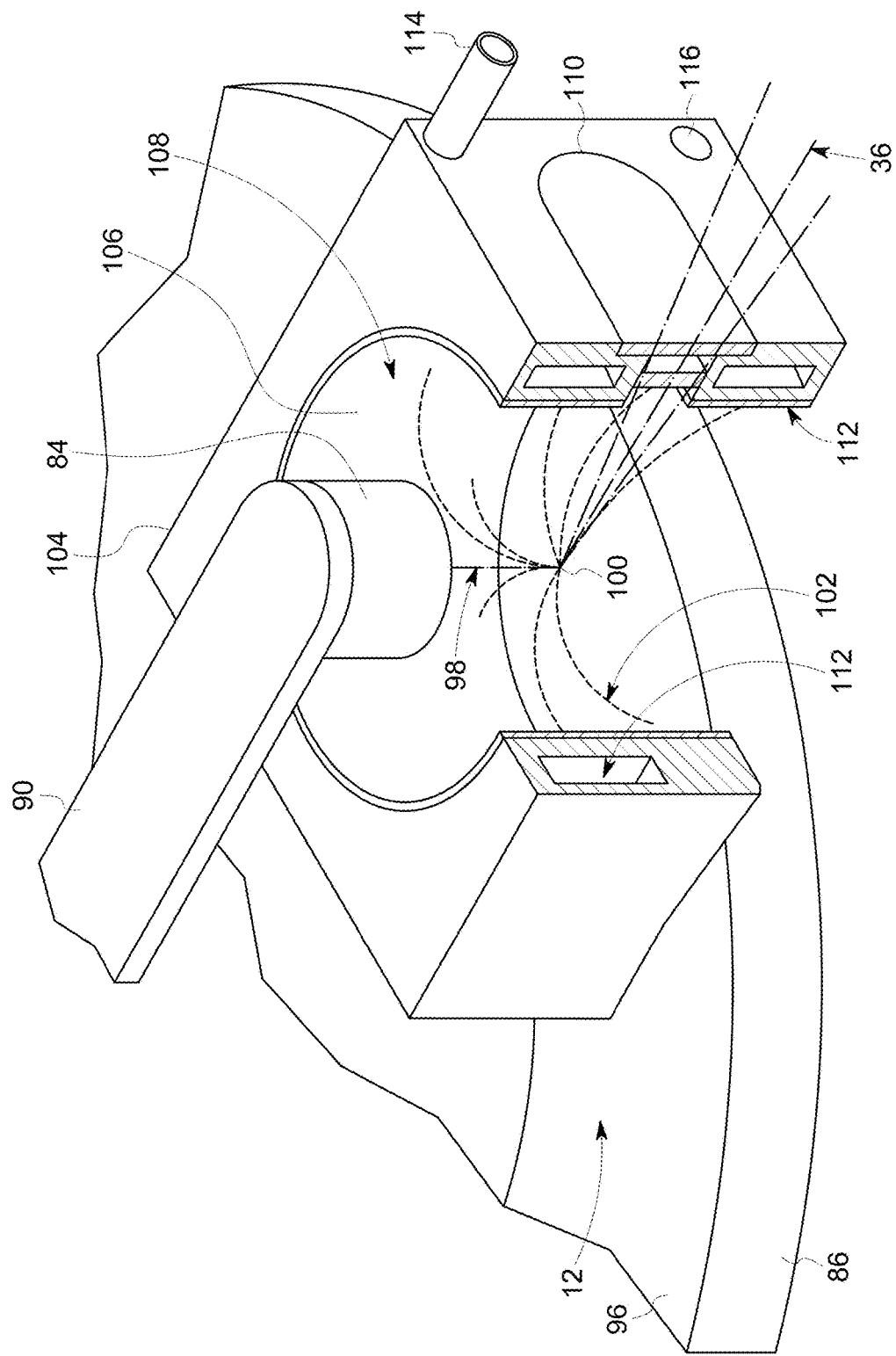
Figure 6:
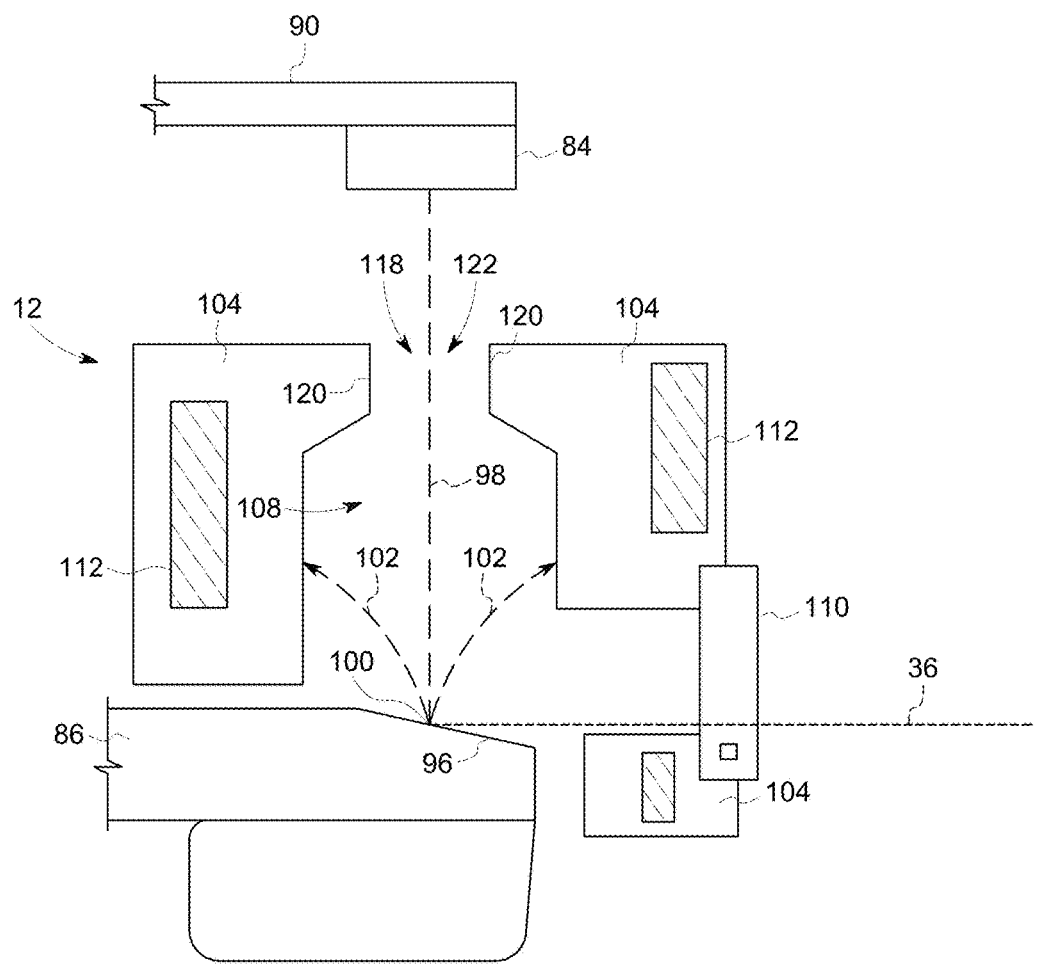
Figure 7:
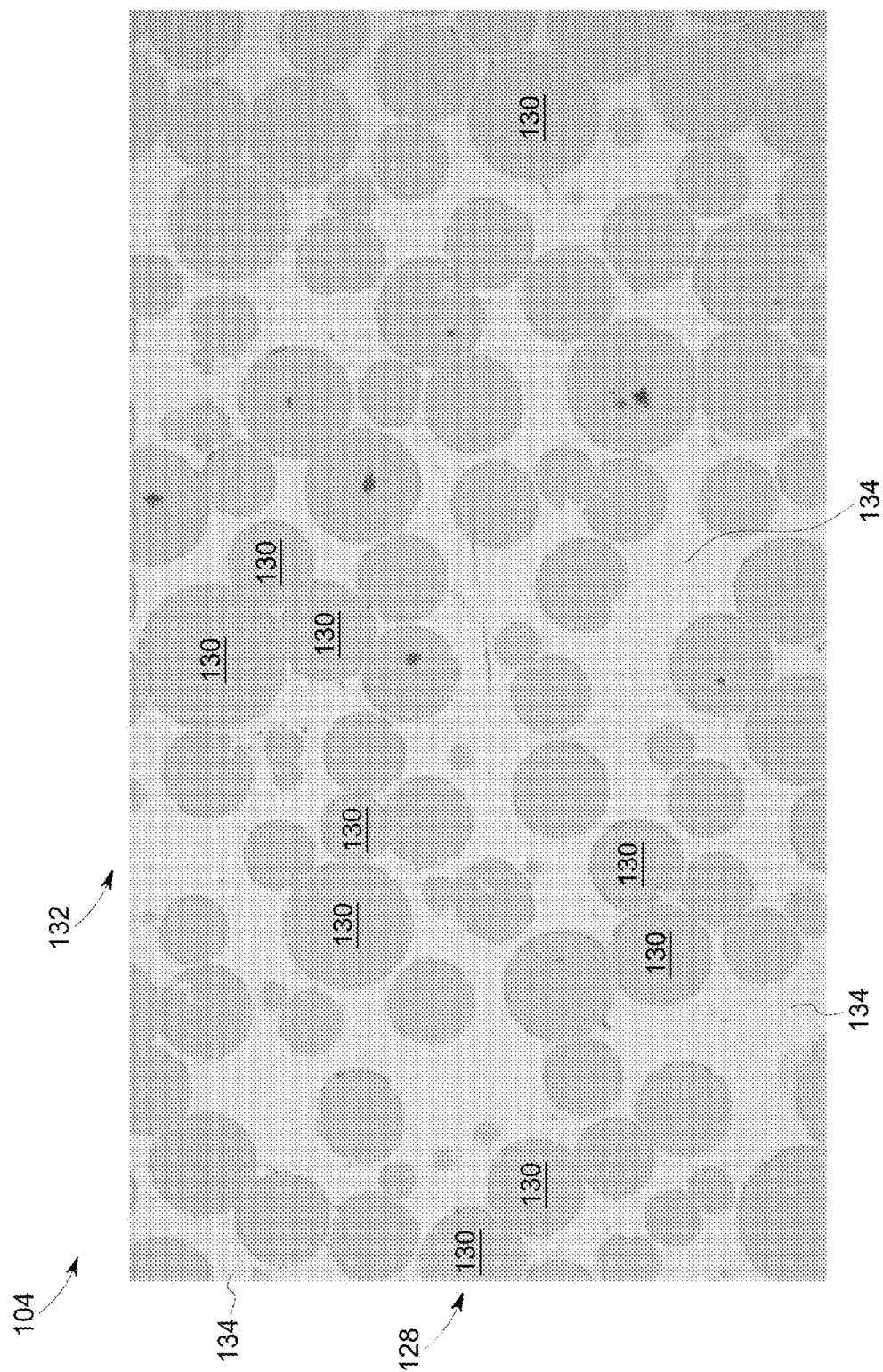
Figure 8:
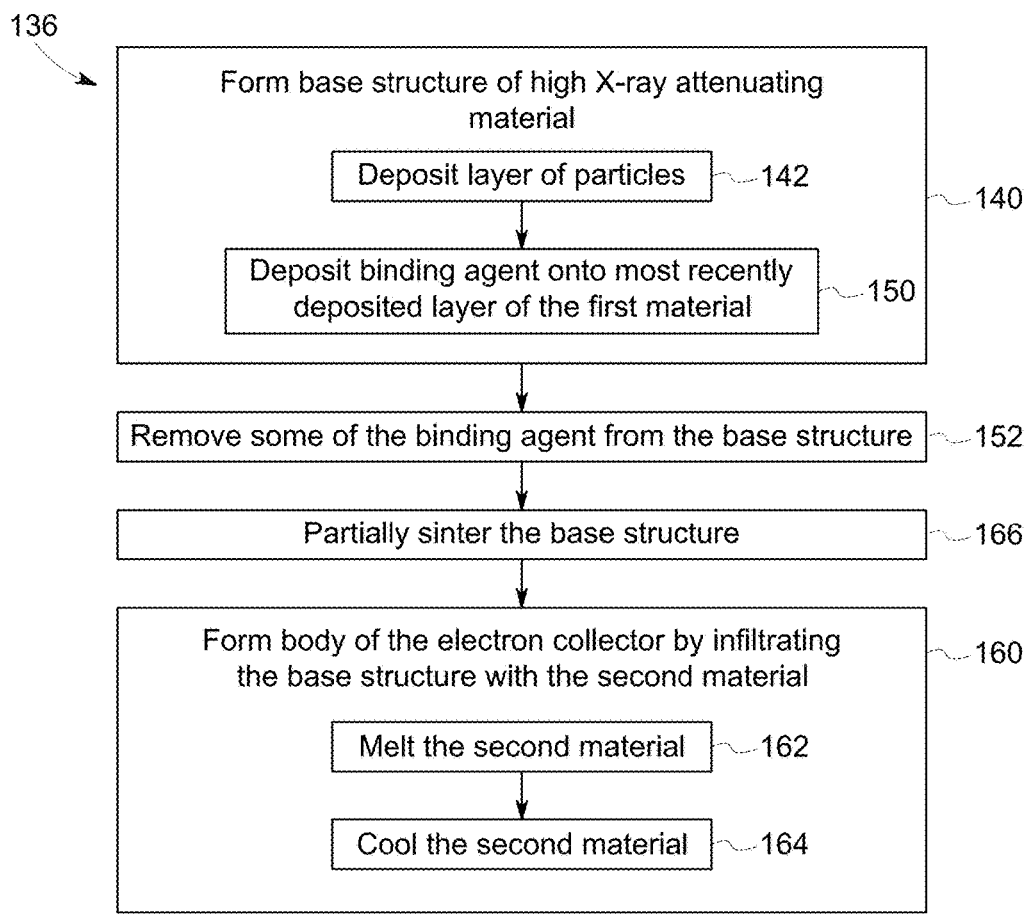
Figure 9:
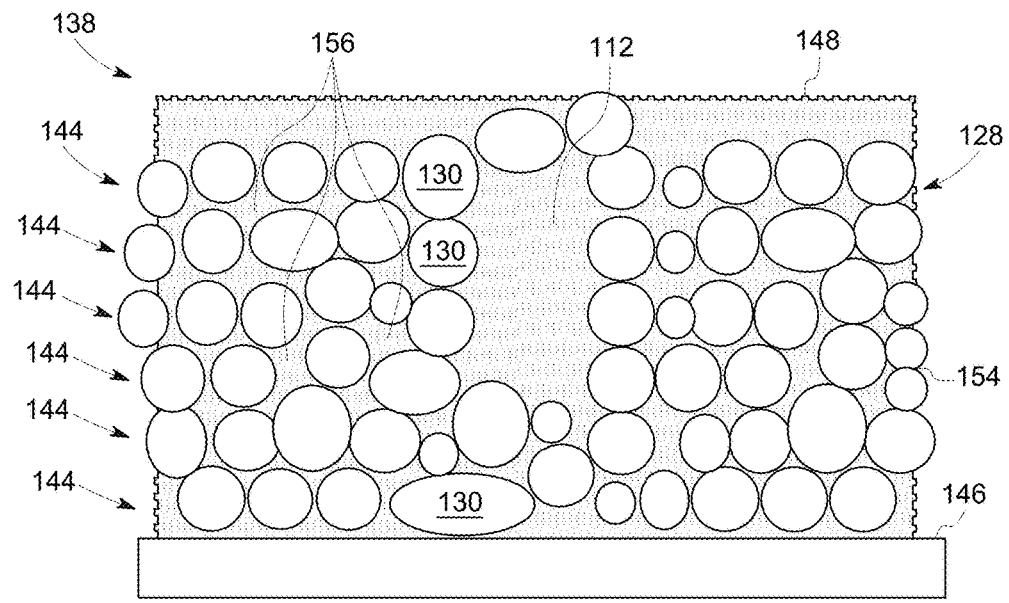
Figure 10:
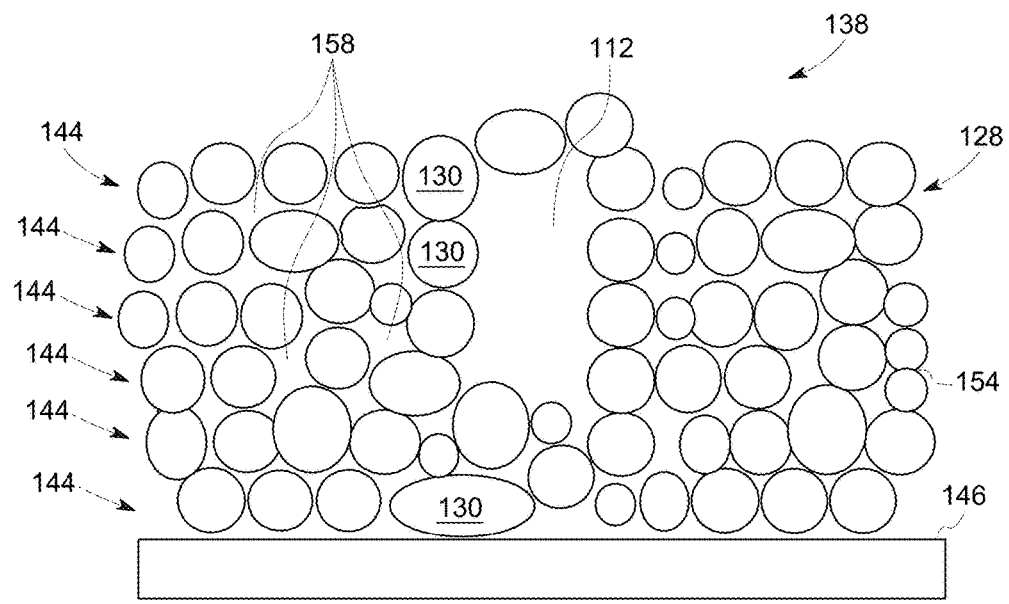

FIG. 4 is a perspective view of the electromagnetic ray generator of FIG. 1, wherein a motor of the electromagnetic ray generator has been exploded to reveal a stator, and wherein a portion of a vacuum vessel of the electromagnetic ray generator and a portion of the stator have been cutaway to reveal an anode of the electromagnetic ray generator mounted to a rotor of the motor, in accordance with an embodiment of the present invention;

FIG. 5 is a close up perspective view of the electron collector disposed within the electromagnetic ray generator of FIG. 4, wherein a portion of the electron collector has been cutaway to reveal a focal point of an electron beam on the anode, in accordance with an embodiment of the present invention;

FIG. 6 is a close up planar view of another embodiment of the electron collector of FIG. 5, wherein the electron collector has a throat, in accordance with an embodiment of the present invention;

FIG. 7 is a microscopic view of a body of the electron collector of FIG. 5, in accordance with an embodiment of the present invention;

FIG. 8 is a flow chart depicting a method for constructing the electron collector of FIG. 5, in accordance with an embodiment of the present invention;

FIG. 9 is a diagram of a base structure formed during the method of FIG. 8, in accordance with an embodiment of the present invention; and FIG. 10 is another diagram of the base structure of FIG. 9, wherein the base structure has been made porous during the method of FIG. 8, in accordance with an embodiment of the present invention.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "imaging procedure" and/or "medical imaging procedure" refer to a medical procedure that involves an imaging system to assist in accomplishing one or more tasks such as deploying/installing a stent into a blood vessel, locating an ulcer, imaging a clogged artery, suturing a patient, and/or other medical processes. The term "vacuum," as used herein, means a pressure of about zero (0) psi.

Additionally, while the embodiments disclosed herein are described with respect to an x-ray based imaging system, e.g., a computed tomography ("CT") imaging system, it is to be understood that embodiments of the present invention are equally applicable to other devices and/or imaging systems which generate electromagnetic waves/radiation via striking an anode with an electron beam. Further, embodiments of the present invention related imaging systems may be used to analyze objects within any material which can be internally imaged, generally. As such, embodiments of the present invention are not limited to analyzing objects within human tissue.

Referring now to FIG. 1, the major components of an imaging system 10 that includes an electron collector 12 (FIG. 4), in accordance with an embodiment of the present invention, is shown. As will be understood, while the imaging system 10 is depicted in the accompanying drawings as a CT imaging system, as stated above, in embodiments, the imaging system 10 may be any imaging system and/or device that generates electromagnetic rays by striking an anode with an electron beam. Accordingly, as shown in FIG. 1, the imaging system 10 includes a detector assembly 14 that is utilized to scan a patient 16, and a controller 18, which includes at least one processor 20 and a memory device 22. The controller 18 may electronically communicate with the detector assembly 14 via one or more communication links 24 over which data generated by the detector assembly 14 may be passed to the controller 18. As will be appreciated, in embodiments, the system 10 may further include a human-machine interface ("HMI") 26, i.e., a work station, that provides for a user/technologist/physician to interact with the imaging system 10. The imaging system 10 may further include a table 28 for supporting the patient 16 during scanning procedures.

Figure 2:
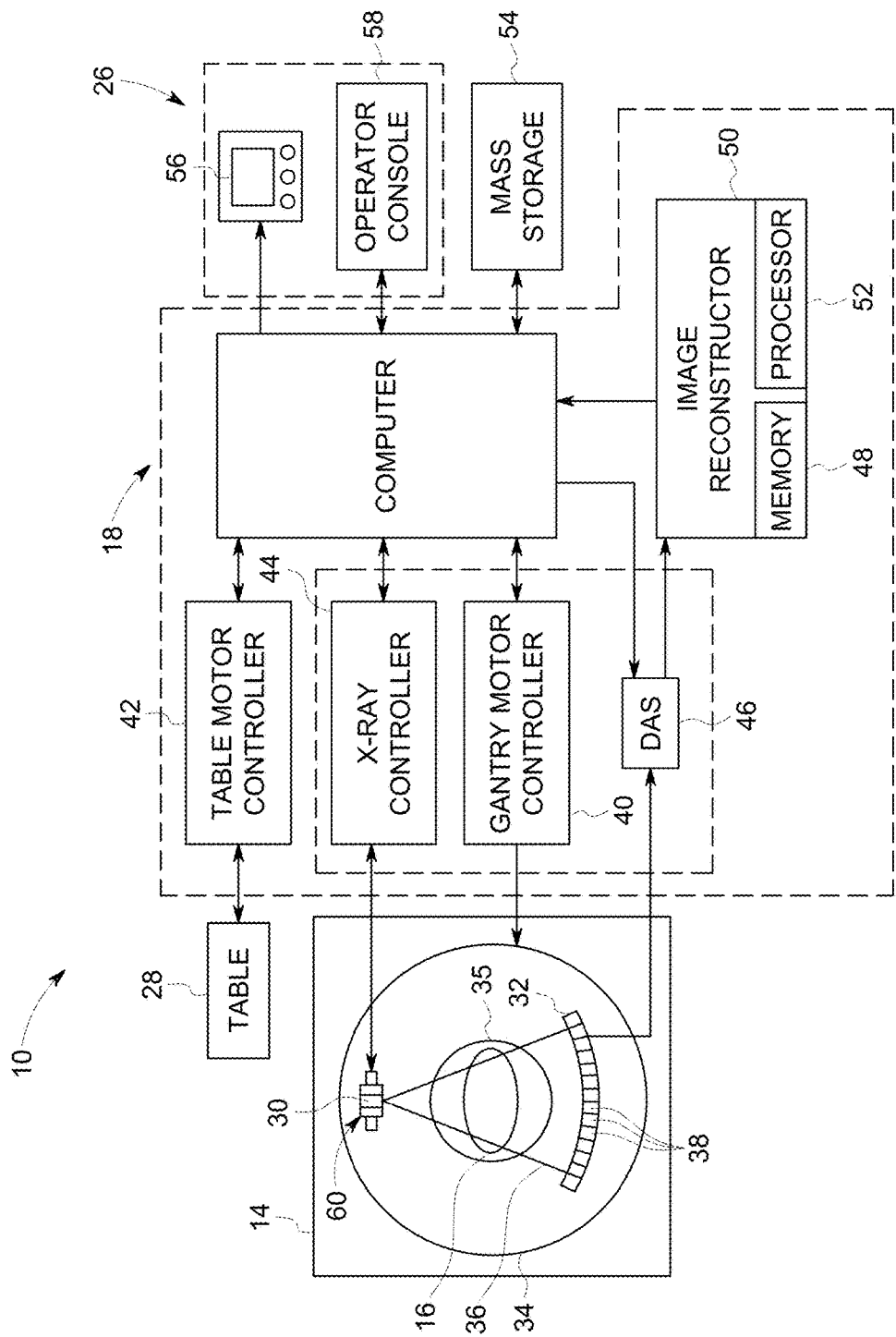
FIG. 2 is a block diagram of the imaging system of FIG. 1, in accordance with an embodiment of the present invention.

As illustrated in FIG. 2, the detector assembly 14 may include an electromagnetic ray generating device/ray generator 30 and a radiation detector 32 disposed within a rotating gantry 34 opposite one another. As will be understood, the patient 16 is positioned within a bore 35 of the gantry 34, and x-rays 36 generated/projected by the electromagnetic ray generator 30 are received by the radiation detector 32 after having passed through the patient 16 while the gantry 34 rotates about the patient 16. The radiation detector 32 may include an array of detector elements 38, each of which produces an electric signal representative of an impinging x-ray 36 beam. While the rays 36 generated by the electromagnetic ray generator 30 are disclosed herein as being x-rays, it will be understood that, in embodiments, the rays 36 may be other types of electromagnetic rays/waves, e.g., gamma rays, infrared waves, radio waves, etc.

The controller 18 may include a gantry motor controller 40, a table motor controller 42, a ray controller 44, and a data acquisition system ("DAS") 46. The table motor controller 42 governs actuation of a motor that moves the table 28 in relation to the detector assembly 14, the gantry motor controller 40 controls the rotational direction and/or speed of the gantry 34, the ray controller 44 provides power and timing signals to the ray generator 30, and the DAS 46 samples analog projection data from the detector elements 38 and converts the analog data to digital projection data for subsequent processing. For example, in embodiments, the digital projection data may be loaded from the DAS 46 into a memory 48 device of an image reconstructor 50 where it is used by a processor 52 to reconstruct one or more images via a reconstruction algorithm. The one or more images may then be sent to the HMI 26 and/or a mass storage device 54, e.g., a large computerized data storage apparatus such as a network attached storage ("NAS") device.

The HMI 26 includes a monitor 56 for displaying the reconstructed images, and a console 58, e.g., buttons, dials, a touch screen, a keyboard, and/or a mouse, for receiving command/scanning parameters from an operator of the system 10.

Figure 3:
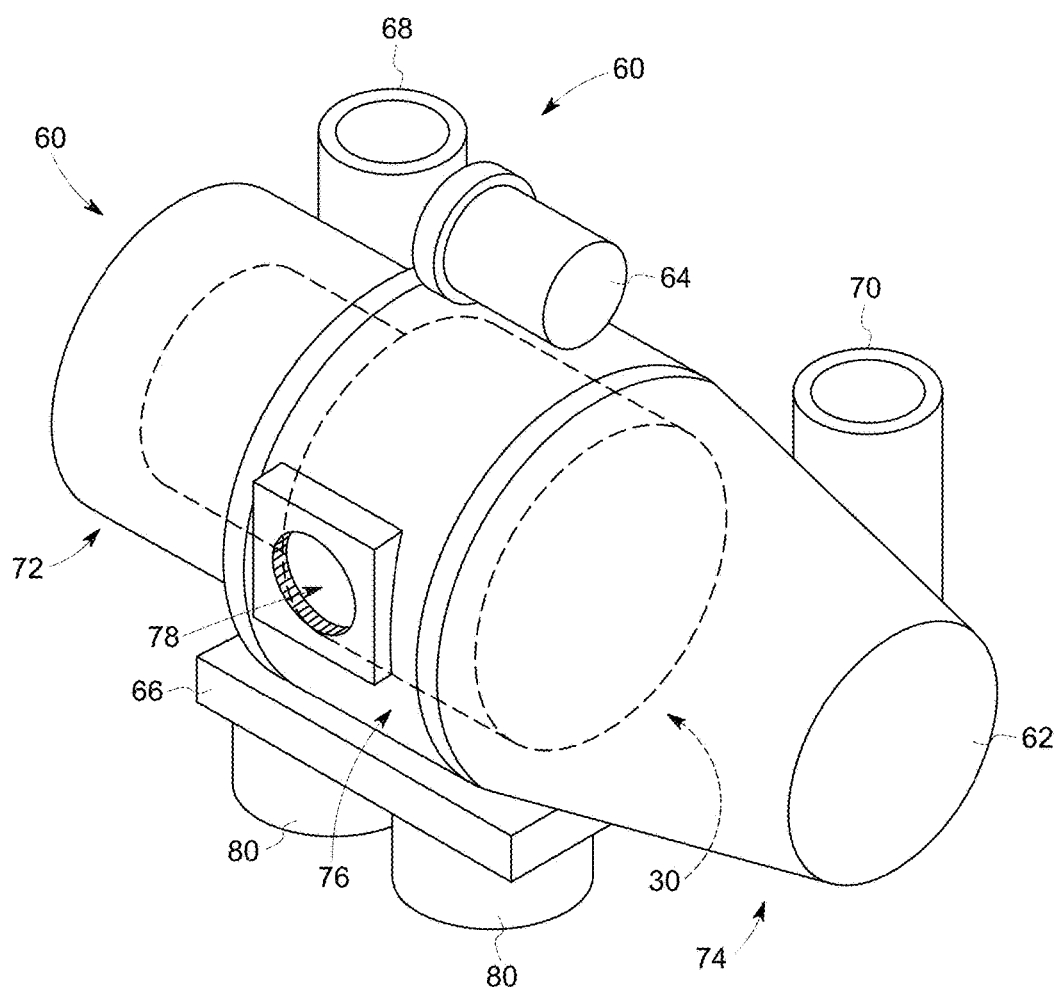
FIG. 3 is a diagram of a housing unit for the electromagnetic ray generator of FIG. 1, in accordance with an embodiment of the present invention.

Turning now to FIG. 3, the ray generator 30 may be disposed within a housing unit 60 which may include a container 62, a pump 64, a radiator 66, an anode receptacle 68, and/or a cathode receptacle 70.

The container 62 may be formed from lead and have an anode end 72, a cathode end 74, and a center section 76 disposed therebetween with an aperture/window 78. The ray generator 30 may be contained within the container 62 such that the generated rays 36 (FIG. 2) are able to pass through the aperture 78. The container 62 may be filled with air or a fluid, e.g., dielectric oil/transformer oil which, as will be discussed in greater detail below, is circulated throughout the container 62 via the pump 64 so as to cool/transfer heat away from the ray generator 30.

The radiator 66 may be disposed to one side of the center section 76 and fluidly connected to the interior of the container 62 such that the radiator 66 is able to cool the fluid by absorbing and radiating heat from it into the surrounding atmosphere. As shown in FIG. 3, in embodiments, the radiator 66 may include one or more fans 80 for providing a cooling air flow over the radiator 66 as the fluid circulates through it.

The anode 68 and cathode 70 receptacles serve as conduits through which electrical connections may be made to the ray generator 30 within the container 62.

Moving to FIG. 4, the ray generator 30 includes a vacuum enclosure/vessel 82 within which a vacuum and/or a near vacuum is maintained. The ray generator 30 further includes a cathode 84, an anode 86, and the electron collector 12, all of which are disposed within the vacuum vessel 82. The vacuum vessel 82 further includes an aperture 88 that aligns with the aperture 78 (FIG. 3) of the container 62 (FIG. 3). In embodiments, the electron collector 12 may partially protrude from the vacuum vessel 82 such that the vacuum within the vessel 82 is maintained. The cathode 84 may be mounted to the vacuum vessel 82 via an arm 90 and positioned such that it faces the anode 86. The anode 86 may be configured to rotate in relation to the cathode 84. For example, in embodiments, the ray generator 30 may further include a motor formed by a stator 92 fastened to the vacuum vessel 82 and a rotor 94 mounted to the anode 86. As will be appreciated, the motor may be electric, pneumatic, or hydraulic, and/or disposed within a casing 95 that may be mounted to the vacuum vessel 82. The anode 86 may be a circular disk with a target track 96, e.g., a tungsten ring, disposed along the circumference of the anode 86 which aligns with the cathode 84. As will be appreciated, while the figures provided herein depict the ray generator 30 as including the vacuum vessel 82, it will be understood that, in other embodiments, the ray generator 30 may not include the vacuum vessel 82.

Turning to FIG. 5, in operation, a voltage is maintained between the cathode 84 and the anode 86 such that an electron beam 98, i.e., a continuous stream of individual electrons, is generated/produced by/at the cathode 84 and strikes the anode 86 at a focal point 100 that falls within the target track 96. Upon striking the anode 86, the kinetic energy of some of the electrons within the electron beam 98 is converted into electromagnetic waves, i.e., the x-rays 36, which radiate out in all directions from the focal point 100. The focal point 100 and/or anode 86, however, may be located within the vacuum vessel 82 (FIG. 4) so as to increase the likelihood that individual x-rays 36 generated by the electrons striking the focal point 100 will pass through the apertures 78 (FIG. 3) and 88 (FIG. 4). As will be appreciated, the striking of anode 86 by the electron beam 98 generates heat within the portion of the anode 86 occupying the focal point 100. Accordingly, in embodiments, the anode 86 may be rotated by the rotor 94 so that the point of the target track 96 aligning with the focal point 100 shifts over time to provide points of the target track 96 an opportunity to cool in between cycles of being struck by the election beam 98.

As will be understood, some of the electrons 102 within the beam 98 backscatter away from the focal point 100 after striking the anode 86. In particular, some of the backscattered electrons 102 will be additionally deflected about ninety degrees (90°) or more by the negative electric charge of the electron beam 98 and/or cathode 84, and thus follow a curved path that re-strikes the anode 86 at a point other than the focal point 100, which, without the electron collector 12, would generate off-focal electromagnetic rays and/or additional/unwanted heat within the anode 86.

Accordingly, the electron collector 12 has a body 104 that includes/defines a surface/interface 106 configured to intercept the backscattered electrons 102 so as to prevent them from re-striking the anode 86. For example, as shown in FIG. 5, the surface 106 may have a shape, e.g., cylindrical, spherical, rectangular, etc., that occupies space intercepting possible trajectories/paths of the backscattered electrons 102. In embodiments, the surface 106 defines a cavity 108 within which the electron beam 98 strikes the anode 86. As will be understood, backscattered electrons 102 that intercept/strike the surface 106 are subsequently absorbed by the body 104 such that their kinetic energy is transformed into heat.

As will be appreciated, the body 104 may also serve as a collimator with respect to the x-rays 36 emitted from the anode 86. For example, as further shown in FIG. 5, the body 104 may include an aperture 110 that aligns with apertures 78 (FIG. 3) and 88 (FIG. 4) such that x-rays 36 having a trajectory/path aligned with the apertures 78, 88, and 110 may pass through the body 104, vacuum vessel 82 (FIG. 4), and fluid container 62 (FIG. 3), while x-rays 36 having trajectory/paths not aligned with the apertures 78, 88, and 110 are restricted from passing through the body 104. In embodiments, the electron collector 12 collimates the generated x-ray 36 such that the x-rays 36 passing through the apertures 78, 88, and 110 define a beam with a sharp edge. In certain aspects, the electron collector 12 may include additional radiation shielding, e.g., lead, in the casing of an insert that surrounds the ray generator 30.

In certain aspects, the body 104 may include one or more internal cooling passageways/heat exchangers 112 which may be fluidly connected to one or more ports 114, 116 disposed within the electron collector 12 such that the fluid, e.g., transformer oil, from the fluid container 62 (FIG. 4), or other source, may flow through the internal passageways 112 and cool the body 104. For example, the pump 64 (FIG. 3) may circulate the fluid through a circuit that includes the pump 64, ports 114, 116, and passageways 112. The passageways 112 may be fabricated to be hermetically sealed, i.e., vacuum tight, with respect to the fluid and the body 104, and/or so as to maximize heat transfer between the fluid and body 104. For example, in embodiments, the passageways 112 may utilize surface augmentation, e.g., fins, roughened walls, and/or have tortuous fluid flow paths. For example, the internal passageways 112 may have integrated turbulence flow enhancements that provide for enhanced turbulent convention heat transfer. Further, the passageways 112 may also be designed to maximize the ratio of surface area to volume and/or to minimize pressure drop of the fluid while providing for maximum heat transfer between the fluid and the body 104. As the passageways 112 are formed directly in the body 104, in embodiments, there are no braze/weld joints for sealing the passageways/heat exchangers 112, as is commonplace in the manufacture of traditional electron collectors. As will be appreciated, the elimination of such braze/weld joints reduces and/or eliminates the opportunity for leaks and failure of vacuum in the vessel 82.

As illustrated in FIG. 6, in embodiments, the body 104 of the electron collector 12 may form a throat 118, i.e., an elongated portion 120 of the body 104 having an opening 122 fluidly connected to the cavity 108. Accordingly, in embodiments, the cathode 84 may be disposed outside of the cavity 108 and/or body 104 such that the electron beam 98 enters the throat 118 via the opening 122 and passes through the elongated portion 120 prior to entering the cavity 108 and striking the anode 86.

Moving to FIG. 7, the body 104 of the electron collector 12 is formed by particles 128 of a first material 130 disposed within a matrix 132 of a second material 134. As used herein, the term "matrix" refers to a structure that contains and restricts the movement of particles such that the structure and the particles form a homogeneous, or substantially homogeneous, solid. In other words, the particles 128 may be continuously and/or isotropically distributed throughout the matrix 132. In embodiments, movement of the particles 128 may be restricted by the matrix 132 without chemical bonding between the first 130 and second 134 materials, e.g., the first 130 and second 134 materials may or may not be alloyed together. The first 130 and/or second 134 materials may have qualities that aid the electron collector 12 in absorbing backscattered electrons 102, conducting heat, blocking/collimating the x-rays 36, and/or other qualities conducive for managing, controlling, and/or otherwise manipulating the backscattered electrons 102 and/or the x-rays 36. The materials 130, 134 may also be selected so as to provide: improved ductility; tensile strength; weld-ability and/or braze-ability to additional components made from stainless steel, kovar, copper, nickel, other metals, and/or alloys thereof; to lower the mass of the body 104; and/or to reduce manufacturing/fabrication costs of the electron collector 12.

For example, in embodiments, the first material 130 may have a higher x-ray attenuation coefficient than the second material 134, and/or the second material 134 may have a higher thermal conductivity than the first material 130. As will be understood, in other embodiments, the second material 134 may have a higher attenuation coefficient than the first material 130, and/or the first material 130 may have a higher thermal conductivity than the second material 134. Accordingly, in embodiments, the first material 130 includes at least one of tungsten, molybdenum, tantalum, and alloys thereof; and/or the second material 134 includes at least one of copper, aluminum, and alloys thereof.

Therefore, as will be appreciated, the first material 130 may facilitate the majority of the attenuation/columniation of the x-rays 36 by the electron collector 12, while the second material 134 facilitates the majority of the heat conduction within the electron collector 12. Moreover, as the distribution of the particles 128 of the first material 130 within the matrix 132 formed by the second material 134 is homogenous, or substantially homogenous, in embodiments, the ability to attenuate/collimate the x-rays 36 and conduct heat is substantially the same over the entirety of the body 104.

Referring now to FIGS. 8-10, a flow chart depicting a method 136 of constructing/manufacturing the electron collector 12 and a base structure 138 made during the method 136, in accordance with an embodiment of the invention, are shown. In embodiments, the method 136 may be performed via an additive manufacturing process such as binder jet. Accordingly, the method 136 includes forming 140 the base structure 138 by depositing 142 one or more layers 144 of the particles 128 of the first materials 130 onto a substrate 146, where the layers 144 are bound together via a binding agent 148 as best seen in FIG. 9. For example, in embodiments, forming 140 the base structure 138 may include repeatedly depositing 142 a layer 144 followed by depositing 150 the binding agent 148 onto the most recently deposited 142 layer 144 so that the binding agent 148 binds particles 128 of adjacent layers 144 together. In embodiments, the binding agent 148 is deposited 150 such that it prints the two-dimensional ("2D") shape of the intended layer 144 of the three-dimensional ("3D") base structure 138.

The method 136 further includes removing 152 the binding agent 148 from the base structure 138 such that the base structure 138 is made porous as best seen in FIG. 10. As will be understood, because the layers 144 are formed from particles 128, some portions 154 (depicted as the adjoining borders of the particles 128 in FIGS. 9 and 10) of the binding agent 148 will bind particles 128 together, while other portions 156 (FIG. 9) of the binding agent 148 will not. By removing 152 the non-binding portions 156 (FIG. 9) of the binding agent 148 from the base structure 138, small channels 158 (FIG. 10) between the particles 128 are formed/created, i.e., the base structure 138 is made porous. Removal 152 of the non-binding portions 156 may be accomplished via exposing the non-binding portions 156 to a substance that dissolves the binding agent 148. In other embodiments, removal 152 of the non-binding portions 156 may accomplished via melting and/or burning the non-binding portions 156 away/out of the base structure 138. In yet other embodiments, removal 152 of the non-binding portions 156 may be accomplished in a vacuum furnace in which the non-binding portions 156 are burned out and/or otherwise evaporated.

The method 136 further includes forming 160 the body 104 (FIG. 7) of the electron collector 12 by infiltrating the porous base structure 138 with the second material 134 (FIG. 7) such that the second material 134 forms the matrix 132 (FIG. 7) with the particles 128 disposed therein. For example, in embodiments, the first material 130 may have a higher melting point than the second material 134. Thus, in such embodiments, forming 160 the body 104 may include melting 162 the second material 134 so that it flows into the channels 158 of the base structure 138, and then cooling 164 the second material 134 to a solid state so as to form the matrix 132. As will be understood, in embodiments, the melted second material 134 may flow into the channels 158 via capillary action. As will be further understood, the passageways 112 are not drawn to scale in FIGS. 9 and 10 and, in embodiments, are large enough so that the second material 134 does not block/prevent flow of a fluid through the passageways 112.

In embodiments, the volume ratio/percentage of the first material 130 to the second material 134 may vary from about thirty to seventy (30:70) to about seventy to thirty (70:30). For example, in embodiments, the ratio of the first material 130 to the second material 134 may be about fifty percent (50%) to about fifty percent (50%). Thus, some embodiments may have a body 104 formed from fifty percent (50%) tungsten and fifty percent (50%) copper with an average density of about 14 g/cm$^3$. Further, the thickness of the body 104 can be varied depending on radiation shielding, heat storage, and/or heat transfer requirements at different locations within the body 104. As will be appreciated, the ratio of the first material 130 to the second material 134 may be altered by varying the maximum size of the particles 128, e.g., the smaller/larger the size of the particles 128, the higher/lower the amount of the first material 130 within the matrix 132. Accordingly, in embodiments, the maximum size of the particles 128 may range from about twenty (20) microns to about one hundred (100) microns. For example, in embodiments, the maximum size of the particles 128 may be about 0.1 mm.

Further, in embodiments, the method 136 may further include sintering and/or partially sintering 166 the base structure 138 prior to forming 160 the body 104 (FIG. 7), e.g., the base structure 138 may be subjected to high heat and/or pressures such that the particles 128 of the first material 130 partially sinter together. As will be appreciated, sintering and/or partially sintering 166 the particles 128 of the first material 130 together may improve the strength of the body 104 while still allowing the second material 134 to infiltrate the porous base structure 138.

Finally, it is also to be understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, an electron collector for an electromagnetic ray generating device is provided. The electron collector includes a body having a surface configured to intercept backscattered electrons produced by an electron beam striking an anode to generate electromagnetic rays. The body is operative to absorb the backscattered electrons and is formed by particles of a first material disposed within a matrix of a second material. In certain embodiments, the first material has a higher attenuation coefficient than the second material, and the second material has a higher thermal conductivity than the first material. In certain embodiments, the first material has a higher melting point than the second material. In certain embodiments, the first material includes at least one of tungsten, molybdenum, tantalum, and alloys thereof. In certain embodiments, the second material includes at least one of copper, aluminum, and alloys thereof. In certain embodiments, the body includes at least one internal cooling passageway. In certain embodiments, the body further includes an aperture operative to allow the electromagnetic rays to pass through the body. In certain embodiments, the surface defines a cavity, the electron beam is generated outside of the cavity and strikes the anode within the cavity, and the electron collector further includes a throat defined by the body and operative to allow the electron beam to enter the cavity. In certain embodiments, the body is vacuum tight. In certain embodiments, the electromagnetic rays are x-rays.

Other embodiments provide for an electromagnetic ray generating system. The system includes an anode, a cathode, and an electron collector. The cathode is operative to generate an electron beam that strikes the anode to generate electromagnetic rays; and the electron collector is operative to absorb backscattered electrons produced by the electron beam striking the anode, and is formed by particles of a first material disposed within a matrix of a second material.

Yet still other embodiments provide for an electromagnetic ray generating system. The system includes a vacuum enclosure, an anode disposed within the vacuum enclosure, a cathode disposed within the vacuum enclosure, and an electron collector disposed within the vacuum enclosure. The cathode is operative to generate an electron beam that strikes the anode to generate electromagnetic rays; and the electron collector is operative to absorb backscattered electrons produced by the electron beam striking the anode, and is formed by particles of a first material disposed within a matrix of a second material. In certain embodiments, the first material has a higher attenuation coefficient than the second material, and the second material has a higher thermal conductivity than the first material. In certain embodiments, the first material has a higher melting point than the second material. In certain embodiments, the electron collector includes an aperture operative to allow the electromagnetic rays to pass through the electron collector.

Yet still other embodiments provide for a method of manufacturing an electron collector. The method includes forming a base structure by depositing one or more layers of particles of a first material onto a substrate. The one or more layers are bound together via a binding agent deposited in-between adjacent layers of the one or more layers, and the base structure includes a surface configured to intercept backscattered electrons produced by an electron beam striking an anode to generate electromagnetic rays. The method further includes removing some of the binding agent from the base structure such that the base structure is porous. The method further includes forming a body of the electron collector by infiltrating the porous base structure with a second material such that the second material forms a matrix with the particles of the first material disposed therein. The body is operative to absorb the backscattered electrons. In certain embodiments, the first material has a higher attenuation coefficient than the second material, and the second material has a higher thermal conductivity than the first material. In certain embodiments, the first material includes at least one of tungsten, molybdenum, tantalum, and alloys thereof. In certain embodiments, the second material includes at least one of copper, aluminum, and alloys thereof. In certain embodiments, forming a base structure by depositing one or more layers of particles of a first material onto a substrate includes forming at least one internal cooling passageway within the base structure. In certain embodiments, the electromagnetic rays are x-rays.

Accordingly, as will be appreciated, by utilizing a body formed by particles of a first material contained within a matrix of a second material, some embodiments of the present invention provide for a monolithic electron collector that has improved heat conduction and x-ray attenuation capabilities over traditional electron collectors. Accordingly, some embodiments of the present invention reduce the amount of, and/or eliminate altogether the need for, radiation shielding disposed within an x-ray tube casing at a distance from the focal spot beyond the electron collector. In other words, since the surface/sphere intercepting the possible trajectories of the x-rays from the focal point becomes smaller as the distance from the surface/sphere to the focal point decreases, some embodiments of the present invention reduce the amount of collimating and/or radiation shielding material required to adequately shield the patient and/or operator from x-rays not forming part of the desired beam, as compared to the collimators in many traditional x-ray tubes which are often separate from, and disposed at greater distances from the focal point than, the electron collector.

Moreover, the homogeneous, or substantially homogenous, distribution of a material with a high attenuation coefficient within the body in some embodiments provides for an electron collector with reduce radiation leakage and/or improved hermeticity as compared to traditional electron collectors formed from separate collimators and heat exchanging components joined together via brazing and/or other traditional fabrication methods. Further by fabricating internal cooling passageways directly into the body, some embodiments do not require separate collimation and heat exchanging components fastened via brazed joints, which as stated above, often have reduced heat transfer effectiveness within the body. As will be appreciated, the structure of the body of the electron collector, in some embodiments, provides simultaneously optimized functions of high thermal conductivity, excellent radiation shielding/collimation, and ease of 3D integral heat exchanger passages. Thus, some embodiments provide for an electron collector that has improved internal heat conduction over traditional electron collectors. Further still, by incorporating a radiation shielding material directly into a body, some embodiments reduce radiation damage to the magnets disposed on and/or near the body used to focus an electron beam.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. An electron collector for an electromagnetic ray generating device comprising:
   a body having a surface configured to intercept backscattered electrons produced by an electron beam striking an anode to generate electromagnetic rays, the body operative to absorb the backscattered electrons;
   wherein the body is formed by particles of a first material disposed within a matrix of a second material;
   wherein the first material has a higher attenuation coefficient than the second material, and
   wherein the second material has a higher thermal conductivity than the first material.

2. The electron collector of claim 1, wherein the first material has a higher melting point than the second material.

3. The electron collector of claim 1, wherein the first material includes at least one of tungsten, molybdenum, tantalum, and alloys thereof.

4. The electron collector of claim 1, wherein the second material includes at least one of copper, aluminum, and alloys thereof.

5. The electron collector of claim 1, wherein the body includes at least one internal cooling passageway.

6. The electron collector of claim 1, wherein the body further includes an aperture operative to allow the electromagnetic rays to pass through the body.

7. The electron collector of claim 1, wherein
   the surface defines a cavity;
   the electron beam is generated outside of the cavity and strikes the anode within the cavity; and
   the electron collector further includes a throat defined by the body and operative to allow the electron beam to enter the cavity.

8. The electron collector of claim 1, wherein the body is vacuum tight.

9. The electron collector of claim 1, wherein the electromagnetic rays are x-rays.

10. An electromagnetic ray generating system comprising:
    an anode;
    a cathode operative to generate an electron beam that strikes the anode to generate electromagnetic rays;
    an electron collector operative to absorb backscattered electrons produced by the electron beam striking the anode;
    wherein the electron collector is formed by particles of a first material disposed within a matrix of a second material;
    wherein the first material has a higher attenuation coefficient than the second material, and
    wherein the second material has a higher thermal conductivity than the first material.

11. The electromagnetic ray generating system of claim 10, wherein the first material has a higher melting point than the second material.

12. The electromagnetic ray generating system of claim 10, wherein the electron collector includes an aperture operative to allow the electromagnetic rays to pass through the electron collector.

13. A method of manufacturing an electron collector comprising:
    forming a base structure by depositing one or more layers of particles of a first material onto a substrate, the one or more layers bound together via a binding agent deposited in-between adjacent layers of the one or more layers, the base structure including a surface configured to intercept backscattered electrons produced by an electron beam striking an anode to generate electromagnetic rays;
    removing some of the binding agent from the base structure such that the base structure is porous;
    forming a body of the electron collector by infiltrating the porous base structure with a second material such that the second material forms a matrix with the particles of the first material disposed therein;
    wherein the body is operative to absorb the backscattered electrons.

14. The method of claim 13, wherein
    the first material has a higher attenuation coefficient than the second material, and
    the second material has a higher thermal conductivity than the first material.

15. The method of claim 13, wherein the first material includes at least one of tungsten, molybdenum, tantalum, and alloys thereof.

16. The method of claim 13, wherein the second material includes at least one of copper, aluminum, and alloys thereof.

17. The method of claim 13, wherein forming a base structure by depositing one or more layers of particles of a first material onto a substrate comprises:
    forming at least one internal cooling passageway within the base structure.

18. The method of claim 13, wherein the electromagnetic rays are x-rays.

* * * * *